US00PP20719P2

(12) United States Plant Patent
Meilland

(10) Patent No.: US PP20,719 P2
(45) Date of Patent: Feb. 2, 2010

(54) FLORIBUNDA ROSE PLANT NAMED 'MEISIASTRI'

(50) Latin Name: *Rosa hybrida*
Varietal Denomination: Meisiastri

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/314,185

(22) Filed: Dec. 5, 2008

(51) Int. Cl.
*A01H 5/00* (2006.01)

(52) U.S. Cl. ..... Plt./143
(58) Field of Classification Search ..... Plt./143
See application file for complete search history.

*Primary Examiner*—Annette H Para
(74) *Attorney, Agent, or Firm*—Buchanan Ingersoll & Rooney PC

(57) ABSTRACT

A new and distinct variety of Floribunda rose plant is provided that forms attractive double white blossoms that are striped with purple-rose and pink coloration. The vegetation is vigorous and a tall bushy growth habit with full branching is displayed. The blossoms exhibit a strong, sweet, and tangy fragrance. The plant is particularly well suited for providing distinctive attractive ornamentation in the landscape.

1 Drawing Sheet

Figure 1:
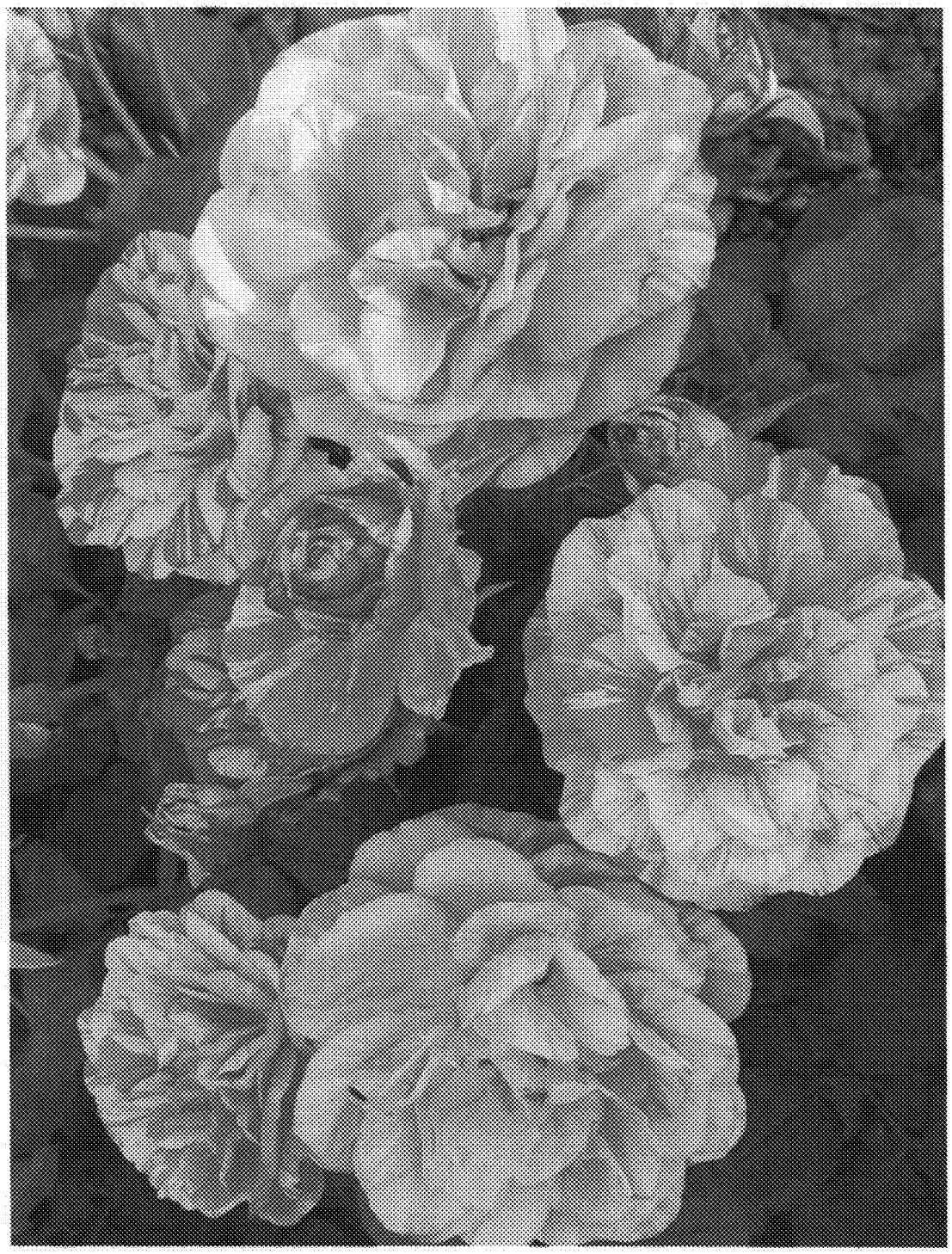

Botanical/commercial classification: *Rosa hybrida*/Floribunda Rose Plant.

Varietal denomination: cv. Meisiastri.

SUMMARY OF THE INVENTION

The new variety of *Rosa hybrida* Floribunda rose plant was created in France by artificial pollination wherein two parents were crossed which previously had been studied in the hope that they would contribute the desired characteristics. The female parent (i.e., the seed parent) was the product of the cross of the 'KORblue' variety (non-patented in the United States) and the 'DELbiop' variety (non-patented in the United States). The male parent (i.e., the pollen parent) was the 'Wekplapep' variety (U.S. Plant Pat. No. 10,126). This 'KORblue' variety is marketed under the SHOCKING BLUE trademark. The 'DELbiop' variety is marketed under the LANCOME trademark. The 'Wekplapep' variety is marketed under the SENTMENTAL trademark. The parentage of the new variety can be summarized as follows:

('KORblue'×'DELbiop')×'Wekplapep'.

The seeds resulting from the above pollination were sown and small plants were obtained which were physically and biologically different from each other. Selective study resulted in the identification of a single plant of the new variety.

It was found that the new Floribunda rose plant of the present invention:

(a) forms vigorous vegetation,
(b) forms a tall bushy upright growth habit with full branching,
(c) forms attractive double white blossoms having a strong fragrance that are striped with purple-rose and pink coloration,
(d) displays new foliage having red-colored veins on the under surface, and
(e) is particularly well suited for providing distinctive attractive ornamentation in the landscape.

The new variety well meets the needs of the horticultural industry and can be grown to advantage in parks and gardens.

The new variety can be readily distinguished from its ancestors. For instance, 'KORblue' variety forms blossoms which display a lilac-mauve coloration. The 'DELbiop' variety is a Hybrid Tea which forms deep pink blossoms having no fragrance. The 'Wekplapep' variety is a Floribunda which forms blossoms having a deep red blend coloration.

Additionally, the new variety can be readily distinguished from the 'Meiroylear' variety (U.S. Plant patent application No. 12/314,187). Unlike the new variety of the present invention, the 'Meiroylear' variety is a Grandiflora that forms blossoms having bright red with yellow stripes finishing to medium pink and cream and commonly assumes a lesser height.

The new variety has been found to undergo asexual propagation at Wasco, Calif., U.S.A., by a number of routes, including budding, grafting, and the use of cuttings. Such asexual propagation by the above-mentioned techniques has shown that the characteristics of the new variety are stable and are strictly transmissible by such asexual propagation from one generation to another.

Accordingly, the new variety undergoes asexual propagation in a true-to-type manner.

The new variety has been named 'Meisiastri', and is being marketed under the JULIO IGLESIAS trademark.

BRIEF DESCRIPTION OF THE PHOTOGRAPH

The accompanying photograph shows as nearly true as it is reasonably possible to make the same, in a color illustration of this character, a typical specimen of the new variety. Blossoms in various stages of development as well as foliage are illustrated. The illustrated plant was approximately two years of age, was budded on 'Dr. Huey' understock (non-patented in the United States), and was being grown outdoors at Wasco, Calif., U.S.A. during October, 2006.

DETAILED DESCRIPTION

The chart used in the identification of the colors is that of The Royal Horticultural Society (R.H.S. Colour Chart) except where ordinary color terms are utilized. Such common color terms are to be accorded their customary dictionary significance. The description is based upon the observation during July of plants of the new variety at an age of approximately two years while budded on 'Dr. Huey' rootstock and grown near West Grove, Pa., U.S.A.

Class: Floribunda.

Plant:

*Growth habit.*—Vigorous, tall and bushy with full branching.

*Height.*—Commonly approximately 1.4 m at an age of two years.

*Width.*—Commonly approximately 1 m at an age of two years.

Branches:

*Color.*—Young stems: near Green Group 139C. adult wood: near Green Group 137D.

*Thorns.*—Size: commonly approximately 8 mm in length on average, and approximately 5 mm in size on average at the base. color: commonly near Greyed-Orange Group 165B.

Leaves:

*Overall appearance.*—Abundant, attractive medium green foliage.

*Leaflets.*—Shape: generally elliptic. number: 3, 5 and 7 (occasionally). apex: acuminate. base: rounded. size: the terminal leaflets commonly are approximately 3.5 to 5 cm in length on average, approximately 3 to 3.5 cm in width on average, and commonly display margins that curl downwards. serration: small and single. texture: smooth on both surfaces with some coarseness at the veins. color: Green Group 137B on the upper surface, and Green Group 146C on the under surface.

Inflorescence:

*Number of flowers.*—Commonly one per stem.

*Peduncle.*—Usually erect, relatively strong, commonly approximately 5 to 7 cm in length, moderately rough with many stipulate glands, and commonly between Yellow-Green Group 144B and Yellow-Green Group 146C in coloration with stems commonly measuring approximately 22 to 38 cm in length on average.

*Sepals.*—Inner surfaces are covered with fine woody tomentum, and the margins commonly are lined with some stipulate glands and hairs.

*Buds.*—Shape: pointed to globular, open well, and commonly are not prevented from opening by wet, cold, hot, or dry weather. length: approximately 1 cm on average. width: approximately 1 cm at the widest point on average. texture: bears numerous stipulate glands. color: Green Group 143C.

*Flower.*—Diameter: approximately 8 cm on average when fully open. color (when opening): upper side: near Red-Purple Group 62D and Red-Purple Group 66C. under side: near Red-Purple Group 62D and Red-Purple Group 63C. color (when fully open): upper side: near Red-Purple Group 67D and White Group 155A. under side: near Red-Purple Group 62D and Red-Purple Group 63C. color stability: with full maturity the purple-rose coloration lightens. fragrance: strong, sweet, and tangy. petal number: commonly approximately 50 on average under normal growing conditions. lastingness: on the plant the blossoms commonly last three to four days or more. petal shape: nearly round to broadly obovate with rounded apices that curve downward, and with the inner petals commonly being narrowly obovate. petal substance: medium thickness. petal texture: on the upper surfaces slightly velvety to satiny, and on the under surfaces moderately velvety to satiny. petal drop: good with the petals commonly detaching cleanly before drying. stamen number: approximately 38 on average. anthers: regularly arranged around the styles, commonly open at approximately the same time, and moderately small for the class. filaments: commonly of uneven lengths, most bear anthers, and near Greyed-Yellow Group 162B in coloration. pistils: commonly approximately 35 on average. styles: commonly near Red Group 45D in coloration. stigmas: commonly near Yellow-Orange Group 19B in coloration. ovaries: commonly enclosed within the calyx. hips: globular, moderately short in length, moderately smooth, with moderately thick fleshy walls, near Yellow-Green Group 145A in coloration, and the sepals tend to fall away from the hips promptly.

Development:

*Vegetation.*—Vigorous.

I claim:

1. A new and distinct Floribunda rose plant characterized by the following characteristics:

(a) forms vigorous vegetation, (b) forms a tall bushy growth habit with full branching, (c) forms attractive double white blossoms having a strong fragrance that are striped with purple-rose and pink coloration, (d) displays new foliage having red-colored veins on the under surface, and (e) is particularly well suited for providing attractive distinctive ornamentation in the landscape;

substantially as shown and described.

* * * * *